US011342722B2

(12) United States Patent
Yu

(10) Patent No.: US 11,342,722 B2
(45) Date of Patent: *May 24, 2022

(54) LASER SYSTEMS AND METHODS

(71) Applicant: Boston Scientific Scimed, Inc., Maple Grove, MN (US)

(72) Inventor: Honggang Yu, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/069,094

(22) Filed: Oct. 13, 2020

(65) Prior Publication Data
US 2021/0044072 A1 Feb. 11, 2021

Related U.S. Application Data

(63) Continuation of application No. 16/008,438, filed on Jun. 14, 2018, now Pat. No. 10,840,666.
(Continued)

(51) Int. Cl.
*H01S 3/00* (2006.01)
*H01S 3/082* (2006.01)
(Continued)

(52) U.S. Cl.
CPC ............ *H01S 3/0071* (2013.01); *A61B 18/26* (2013.01); *G02B 6/4206* (2013.01);
(Continued)

(58) Field of Classification Search
CPC ...... H01S 3/0071; H01S 3/005; H01S 5/4012; H01S 3/082; H01S 3/2383; H01S 3/0085;
(Continued)

(56) References Cited

U.S. PATENT DOCUMENTS 5,387,211 A 2/1995 Saadatmanesh et al.
5,642,370 A 6/1997 Mitchell et al.
(Continued)

FOREIGN PATENT DOCUMENTS

CN 101814693 A 8/2010
EP 3176889 A1 6/2017
WO WO 2013/154708 A1 10/2013

OTHER PUBLICATIONS

International Search Report and Written Opinion for corresponding International Application No. PCT/US2018/037496, dated Sep. 28, 2018 (15 pages).

*Primary Examiner* — Yuanda Zhang
(74) *Attorney, Agent, or Firm* — Bookoff McAndrews, PLLC

(57) ABSTRACT

Laser systems and methods are disclosed. One laser system comprises: a plurality of laser resonators, each resonator being operable to discharge an input laser beam; a relay assembly including at least one curved reflective surface that redirects each input laser beam, and reduces a beam size of the redirected beam; a galvo including a curved reflective surface that receives each redirected beam, and outputs a combined laser beam at power level greater than a power level of each laser input beam; and a coupling assembly that reduces spherical aberrations in the combined laser beam, and directs the combined laser beam into an optical fiber. In this system, the combined laser beam may have a maximum beam parameter product lower than a minimum beam parameter product of the optical fiber. Related systems and methods are also disclosed.

20 Claims, 3 Drawing Sheets

Related U.S. Application Data

(60) Provisional application No. 62/522,428, filed on Jun. 20, 2017.

(51) Int. Cl.
  *H01S 3/23* (2006.01)
  *G02B 27/09* (2006.01)
  *H01S 5/40* (2006.01)
  *A61B 18/26* (2006.01)
  *G02B 6/42* (2006.01)

(52) U.S. Cl.
  CPC ....... *G02B 6/4214* (2013.01); *G02B 27/0905* (2013.01); *H01S 3/005* (2013.01); *H01S 3/082* (2013.01); *H01S 3/2383* (2013.01); *H01S 5/4012* (2013.01); *H01S 3/0085* (2013.01)

(58) Field of Classification Search
  CPC . G02B 6/4206; G02B 6/4214; G02B 27/0905
  See application file for complete search history.

(56) References Cited

U.S. PATENT DOCUMENTS

| | | |
|---|---|---|
| 5,659,563 A | 8/1997 | Reed et al. |
| 7,786,406 B2 | 8/2010 | Flanagan |
| 2006/0182154 A1* | 8/2006 | Tanaka .................... H01S 3/139 372/9 |
| 2015/0293348 A1 | 10/2015 | Waisman et al. |
| 2017/0179683 A1 | 6/2017 | Sakamoto |

* cited by examiner

LASER SYSTEMS AND METHODS

CROSS-REFERENCE TO RELATED APPLICATIONS

This patent application is a continuation under 37 CFR § 1.53(b) of U.S. application Ser. No. 16/008,438, filed Jun. 14, 2018, which claims the benefit of priority under 35 U.S.C. § 119 to U.S. Provisional Patent Application No. 62/522,428, filed Jun. 20, 2017, each of which is herein incorporated by reference in its entirety.

TECHNICAL FIELD

Aspects of the present disclosure generally relate to laser systems and methods regarding the same.

BACKGROUND

One measure of beam quality is a Beam Parameter Product (or "BPP"). The BPP of a laser beam may be equal to the product of beam radius (measured at the beam waist) multiplied by the divergent angle (half-angle) of the beam. A smaller BPP represents a better beam quality. It can be difficult to for lamp pumped laser systems to maintain laser beams having a low BPP, a high pulse energy, and a high frequency due to the thermal lensing effect of the gain medium.

The BPP of the fiber may be equal to the product of the fiber core radius multiplied by the numerical aperture (or "NA") of the fiber. When the BPP of the output laser beam is very close to the BPP of the fiber, a very low alignment tolerance will be expected. Optics commonly used to direct the input laser beam to the optical fiber may further degrade beam quality, making the BPP of the laser beam even closer to the BPP of the fiber, and further reducing alignment tolerances. At high pulse energies and frequencies, low alignment tolerances can make the laser system less reliable.

Aspects of this disclosure address these and related challenges.

SUMMARY

One aspect of this disclosure is a laser system. The laser system may comprise: a plurality of laser resonators, each resonator being operable to discharge an input laser beam; a relay assembly including at least one curved reflective surface that redirects each input laser beam, and reduces a beam size of the redirected beam; a galvo including a curved reflective surface receives each redirected beam, and outputs a combined laser beam at power level greater than a power level of each laser input beam; and a coupling assembly that reduces spherical aberrations in the combined laser beam, and directs the combined laser beam into an optical fiber, wherein the combined laser beam has a maximum beam parameter product lower than a minimum beam parameter product of the optical fiber.

In some aspects, the at least one curved reflective surface of the relay assembly may have a first curvature radius, the curved reflective surface of the galvo may have a second curvature radius, and the first and second curvatures may be different. The first curvature radius may be greater than the second curvature radius. For example, the second curvature radius may reduce spherical aberrations in the combined laser beam. Each input laser beam may be discharged along a beam path comprising: (i) a first distance extending from one resonator of the plurality of laser resonators to the at least one curved reflective surface of the relay assembly; (ii) a second distance extending from the at least one curved reflective surface of the relay assembly to the curved reflective surface of the galvo; and (iii) a third distance extending from the curved reflective surface of the galvo to an optical fiber. The first and second curvature radii may be sized relative to the first, second, and third distances. For example, the first distance may be approximately equal to the second distance; and the third distance may be greater than the sum of the first and second distances.

The coupling assembly may include one aspherical lens or two spherical lenses. The system may further comprise additional optical components located between the galvo and the coupling assembly. The additional optical components may include at least one of: a beam splitter; a beam combiner; a shutter; or a black shield. The coupling assembly may output the combined laser beam onto an input surface of an optical fiber, and the beam parameter product of the combined laser beam may be at least 10% less than a beam parameter product of the optical fiber at the input surface.

The relay assembly may further comprise a flat reflective surface. The at least one curved reflective surface may redirect the input laser beam towards the flat reflective surface, and reduce the beam size of the input laser beam at the flat reflective surface. The flat reflective surface may redirect the input laser beam towards the curved reflective surface of the galvo. According to this aspect, the plurality of laser resonators may be fixed to a surface, and each reflective surface of the relay assembly may be movable in at least two degrees of freedom relative to the surface. Each input laser beam may be discharged along a beam path comprising: (i) a first distance extending from one resonator of the plurality of laser resonators to the first reflective surface; (ii) a second distance extending from the first reflective surface to the second reflective surface; (iii) a third distance extending from the second reflective surface to the reflective surface of the galvo; and (iv) a fourth distance extending from the reflective surface of the galvo to an optical fiber. The first and second curvature radii may be sized relative to the first, second, third, and fourth distances. For example, the first distance may be approximately equal to the second distance, and the third distance may be greater than the sum of the first, second, and third distances.

Another aspect is another laser system. This laser system may comprise: a plurality of laser resonators, each resonator being operable to discharge an input laser beam through a curved output surface; a relay assembly including at least one curved reflective surface that redirects each input laser beam, and reduces a beam size of the redirected beam; a galvo including a flat reflective surface that receives each redirected beam, and outputs a combined laser beam at power level greater than a power level of each laser input beam; and a coupling assembly that directs the combined laser beam into an optical fiber, wherein the combined laser beam has a maximum beam parameter product lower than a minimum beam parameter product of the optical fiber.

This system may comprise a spherical relay lens that reduces a beam size of the combined laser beam on the coupling assembly. The at least one curved reflective surface of the relay assembly may comprise a first curved reflective surface and a second curved reflective surface. For example, a curvature radius of the output surface may be greater than a curvature radius of the first reflective surface; and a curvature radius of the second reflective surface may be greater than the curvature radius of the first reflective surface.

Another aspect of this disclosure is a method. The method may comprise: discharging input laser beams from a plurality of laser generators; directing each input laser beam towards a relay assembly including at least one curved reflective surface that reduces a beam size of the input laser beam, and redirects the beam toward a reflective surface of a galvo; combining the input laser beams, with the reflective surface of the galvo, into a combined laser beam having a power level greater than a power level of each input laser beam; and outputting the combined laser beam to an optical fiber, wherein the combined laser beam has a maximum beam parameter product lower than a minimum beam parameter product of the optical fiber.

According to one aspect of this method, the reflective surface of the galvo may be curved, and the method may comprise further reducing spherical aberrations in the combined laser beam. According to other aspects, the reflective surface of the galvo may be flat, and the method may further comprise discharging each laser input beam through a curved output surface of each laser resonator. The plurality of laser resonators may be fixed to a surface, the at least one curved reflective surface may comprise a first curved reflective surface and a second curved reflective surface, and the method may comprise moving the first and second reflective surfaces into alignment with the plurality of laser resonators. Any such methods may further comprise directing the combined laser beam through a spherical relay lens.

BRIEF DESCRIPTION OF THE DRAWINGS

The accompanying drawings are incorporated in and constitute a part of this specification. These drawings illustrate aspects of the present disclosure that, together with the description provided herein, serve to explain this disclosure as follows.

DETAILED DESCRIPTION

Aspects of the present disclosure are now described with reference to laser systems and methods. Some aspects are described with reference to lithotripsy procedures where an optical fiber is advanced into a body cavity through a scope until a distal end of the fiber is positioned to treat a stone located in the body cavity. References to a particular type of procedure, laser energy, scope, tissue, bodily location, and/or bodily organ are provided for convenience and not intended to limit the present disclosure unless claimed. Accordingly, the concepts described herein may be utilized for any analogous laser system—medical or otherwise.

Numerous axes and directions are described. The axes may form a Cartesian coordinate system with an origin point O. One axis may extend along a longitudinal axis of an element. Directions and relativity may be indicated by the terms "proximal" and "distal," and their respective initials "P" and "D". Proximal refers to a position closer to the exterior of the body or a user, whereas distal refers to a position closer to the interior of the body or further away from the user. Appending the P or D to an element number or arrow signifies a proximal or distal location or direction. Unless claimed, these terms are provided for convenience and not intended to limit the present disclosure to a particular location, direction, or orientation. Unless stated otherwise, terms such as "generally," "about," "substantially," and/or "approximately" indicate a range of possible values that are within +/−5% of a stated value.

As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." Conversely, the terms "consists of" and "consisting of" are intended to cover an exclusive inclusion, such that a device or method that consists of a list of elements includes only those elements.

Figure 1:
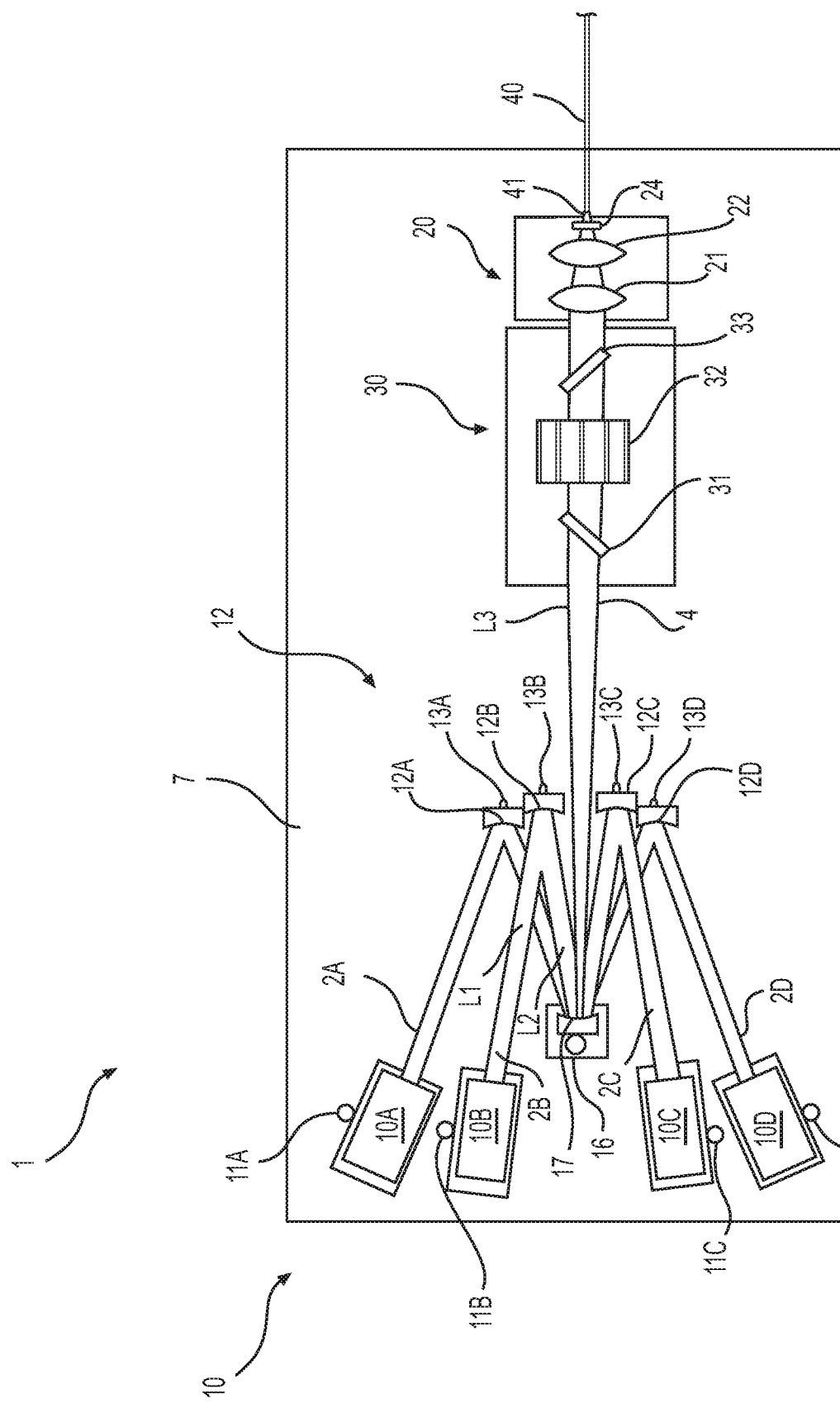
FIG. 1 depicts a laser system according to this disclosure.

As shown in FIG. 1, one aspect of the present disclosure is a laser system 1 including: a plurality of laser resonators 10; a relay assembly 12; and a mirror galvanometer or "galvo" 16 including a movable reflective surface 17. Four laser resonators 10A-D are shown in FIG. 1, although any number may be used. Each laser resonator 10A, 10B, 10C, and 10D is operable to discharge an input laser beam 2A, 2B, 2C, or 2D towards relay assembly 12. As shown, relay assembly 12 includes reflective surfaces that redirect each beam 2A-D towards movable reflective surface 17. Galvo 16 receives each redirected input laser beam 2A-D at reflective surface 17, and outputs a combined laser beam 4 towards an optical fiber 40. Additional optics for controlling, enhancing, and/or delivering beam 4 may be included in laser system 1, such as: a coupling assembly 20 and an optics assembly 30.

As shown in FIG. 1, the plurality of laser resonators 10 may be mounted to a surface 7, such as a table, or an interior surface of a laser console. Laser resonators 10A-D may discharge laser beams 2A-D at a first or input power level. By way of example, an initial BPP of each input laser beam 2A-D at its respective laser resonator 10A-D may be about 48 mm-mrad. The input power level of each beam 2A-D may be same or different. Each laser resonator 10A-D may be movably mounted to surface 7 for precise alignment of input laser beams 2A-D with relay assembly 12. For example, each resonator 10A, 10B, 10C, and 10D of FIG. 1 is mounted on a tilt plate 11A, 11B, 11C, or 11D that is movable with respect to surface 7 in one degree of freedom, such as rotation about an axis transverse to surface 7 (e.g., an X-X or Z-Z axis).

Relay assembly 12 may comprise reflective surfaces configured direct input laser beams 2A-D towards reflective surface 17 of galvo 16. As shown in FIG. 1, relay assembly 12 may include at least one reflective surface positioned in the path of each input laser beam 2A-D. Each reflective surface may be HR coated. Accordingly, relay assembly 12 may comprise a first reflective surface 12A in the path of input laser beam 2A; a second reflective surface 12B in the path of laser beam 2B; a third reflective surface 12C in the path of beam 2C; and a fourth reflective surface 12D in the path of beam 2D. Each reflective surface 12A-D may be movably mounted to surface 7 for precise alignment with resonators 10A-D and galvo 16. In FIG. 1, for example, each reflective surface 12A, 12B, 12C, and 12D may be movably mounted to surface 7 by a tilt mount 13A, 13B, 13C, or 13D. Tilt mounts 13A-D allow for movement of surfaces 12A-D with respect to surface 7 in at least two degrees of freedom, such as rotation about a first axis parallel to surface 7 (e.g., a Y-Y axis), and rotation relative to a second axis transverse to surface 7 (e.g., an X-X or Z-Z axes). Reflective surfaces 12A-D may modify input laser beams 2A-D. For example, each reflective surface 12A-D may be curved to reduce the beam size of input laser beams 2A-D on reflective surface 17.

Galvo 16 may receive laser beams 2A-D from reflective surfaces 12A-D at the input power level, and output combined laser beam 4 at an output power level greater than the input power level of each input laser beam 2A-D. For example, galvo 16 of FIG. 1 may rotate (or otherwise move) reflective surface 17 at different angles so that each one of input laser beams 2A-D is added to combined laser beam 4 at different times, resulting in an output power level that is approximately equal to the sum of each input power level of beams 2A-D. In FIG. 1, for example, if the input power level of each beam 2A-D is approximately equal, then the output power level of combined laser beam 4 will be approximately four times the input power level of each beam 2A-D. The curvature of reflective surfaces 12A-D may cause each input laser beam 2A-D to have spherical aberrations, wherein portions of each beam 2A-D have different focal points. The curvature of reflective surface 17 may reduce such aberrations.

The curvature of reflective surfaces 12A-D may be relative to the curvature of reflective surface 17. For example, the curvature radius of each reflective surface 12A-D may be approximately 165 mm; and the curvature radius of reflective surface 17 may be approximately 500 mm. To reduce the BPP of beams 2A-D and/or beam 4 at various points within system 1, the curvature of reflective surfaces 12A-D and 17 also may be relative to the distances between laser generators 10A-D, relay assembly 12, reflective surface 17, and optical fiber 40. As shown in FIG. 1 with reference to input laser beam 2B, for example: a first distance L1 extends between resonator 10B and reflective surface 12B; a second distance L2 extends between reflective surface 12B and reflective surface 17; and a third distance L3 extends between reflective surface 17 and an input surface 41 of optical fiber 40. The same distances L1, L2, and L3 may be used consistently with beams 2A-D. As shown in FIG. 1, for example, first distance L1 may be approximately 116 mm; second distance L2 may be approximately 110 mm; and third distance L3 may be approximately 283 mm.

Various ratios are defined in this example. These ratios may scaled up or down to accommodate variations of system 1. For example, the curvature radius of reflective surfaces 12A-D may be approximately one third the curvature radius of reflective surface 17; first distance L1 may be approximately equal to second distance L2; and third distance L3 may be greater than the sum of distances L1 and L2.

Laser system 1 may comprise additional optics configured further reduce spherical aberrations, modify laser input beams 2A-D, and/or modify combined laser beam 4. As shown in FIG. 1, for example, coupling assembly 20 and optics assembly 30 may be provided in the path of combined laser beam 4. Coupling assembly 20 may receive combined laser beam 4, reduce spherical aberrations in combined beam 4, and output beam 4 to input surface 41 of fiber 40. Assembly 20 may comprise one or more lenses. In FIG. 1, for example, coupling assembly 20 includes a first spherical lens 21 and a second spherical lens 22. One aspherical lens also may be used. As shown in FIG. 1, coupling assembly 20 may further comprise a black shield 24 that blocks contaminations from fiber misalignment. Black shield 24 may be integral with coupling assembly 20, as in FIG. 1; or separate from coupling assembly 20, as in FIG. 2A.

Optics assembly 30 may comprise: a first beam splitter 31, a shutter 32; and a second beam splitter 33. First beam splitter 31 may redirect a portion of combined laser beam 4 towards a controller (not shown). Shutter 32 may be operable with the controller to provide an automated shut-off switch for system 1. Second beam splitter 33 may receive an aiming laser beam (not shown), and direct the aiming laser beam towards input surface 41 of fiber 40. As shown in FIG. 1, first splitter 31, shutter 32, and second splitter 33 may be located between galvo 16 and coupling assembly 20. Components of optics assembly 30 also may be distributed through laser system 1.

Relay assembly 12 and galvo 16 may improve beam quality by reducing the BPP of input laser beams 2A-D and combined laser beam 4 at various locations within laser system 1. For example, reflective surfaces 12A-D, reflective surface 17, the respective distances L1, L2, and L3 extending therebetween, and coupling assembly 20 may minimize the BPP of combined beam 4 at input surface 41 of optical fiber 40, ensuring high beam quality. Optical fiber 40 may also have a BPP, and the BPP of beam 4 may be lower than the BPP of fiber 40 to increase alignment tolerances within system 1. The BPP of input beam 4 at input surface 41 may be at least 10% less than the BPP of fiber 40 at input surface 41. For example, the BPP of beam 4 at input surface 41 may be approximately 56 mm-rad, and the BPP of fiber 40 at surface 41 may be approximately 68 mm-rad, providing a BPP reduction of approximately 20%.

Alternative and/or additional aspects of laser system 1 are now described with reference to a laser system 100 partially depicted in FIG. 2A, and a laser system 200 partially depicted in FIG. 2B. Systems 100 and 200 are identical to system 1, but-for the modifications shown in FIGS. 2A-B and described below, wherein modified elements are described within the respective 100 or 200 series of numbers. Any aspect of systems 1, 100, and 200 may be interchangeably combined according to this disclosure, each potential combination being part of this disclosure.

Each input laser beam 2A-D may be aligned with reflective surface 117 using four degrees of freedom. In system 1, two degrees of freedom are provided by tilt plates 11A-D, and a further two degrees of freedom by tilt mounts 13A-D. System 100 may eliminate tilt plates 11A-D. For example, system 100 may comprise the plurality of laser resonators 10, a relay assembly 112, and a galvo 116 with a reflective surface 117. The plurality of resonators 10 may be identical to resonators 10A-D described above. An exemplary laser resonator 10A and input laser beam 2A are shown in FIG. 2A for ease of description. Similar configurations may be used for additional input laser beams (e.g., from resonators 10B, 10C, and 10D) in a manner consistent with system 1 of FIG. 1.

Figure 2A:
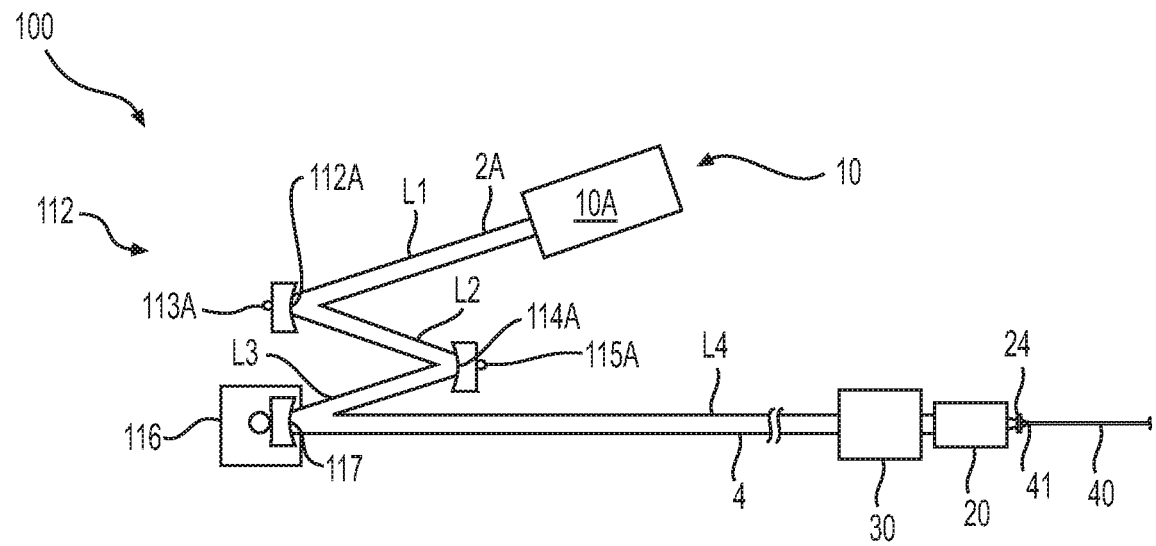
FIG. 2A depicts another laser system according to this disclosure.

As shown in FIG. 2A, relay assembly 112 may comprise: a first reflective surface 112A, and a second reflective surface 114A. First and second reflective surfaces 112A and 114A may provide input laser beam 2A with four degrees of freedom. For example, as shown in FIG. 2A, first reflective surface 112A may be movably mounted to surface 7 by a first tilt mount 113A, and second reflective surface 114A may be movably mounted to surface 7 by a second tilt mount 115A. Similar to above, each tilt mount 113A and 115A may be rotatable in two directions relative to surface 7, providing four degrees of freedom.

The position of laser resonator 10A may be fixed relative to surface 7 in system 100. For example, laser resonator 10A may include a base support with openings, surface 7 may include corresponding openings, and a pin may be inserted into the openings of resonator 10A and surface 7, attaching those elements together. Numerous benefits may be realized with this configuration. For example, because it contains cooling fluids, and high electrical current and/or voltage, the alignment and re-alignment of laser resonator 10A using tilt plates may be difficult and transportation shock vibration may change the laser beam position and pointing. These difficulties are multiplied with each additional input laser beam. By comparison, tilt mounts 113A and 115A may be much easier to align because they support less weight, and the resulting alignment may be easier to maintain because have fewer moving parts. Fixing laser generator 10A relative to surface 7 also makes it easier to replace components of generator 10A, such as the lamp, without disrupting alignments.

As shown in FIG. 2A, laser resonator 10A may discharge input laser beam 2A towards first reflective surface 112A. First reflective surface 112A may modify beam 2A, and redirect the modified beam 2A towards second reflective surface 114A; and second reflective surface 114A may redirect the modified beam 2A towards reflective surface 117. As shown in FIG. 2A, first reflective surface 112A may be a curved; second reflective surface 114A may be a flat; and reflective surface 117 may be curved. As in FIG. 2A, coupling assembly 20 may be included within system 100 to reduce spherical aberrations caused by the curvature of reflective surfaces 112A and 117.

The curvature of reflective surface 112A may be relative to the curvature of reflective surface 117. For example, the curvature radius of surface 112A may be approximately 280 mm; and the curvature radius of reflective surface 117 may be approximately 800 mm. As before, the curvature of reflective surfaces 112A and 117 also may be relative the distances between laser generator 10A, surfaces 112A and 114A, reflective surface 117, and optical fiber 40. In FIG. 2A, for example: a first distance L1 extends between resonator 10A and first reflective surface 112A; a second distance L2 extends between first reflective surface 112A and second reflective surface 114A; a third distance L3 extends between second reflective surface 114A and reflective surface 117; and a fourth distance L4 extends between reflective surface 117 and input surface 41 of optical fiber 40. The same distances L1, L2, L3, and L4 may be used consistently in system 100 for additional input laser beams (e.g., from resonators 10B, 10C, and 10D). As shown in FIG. 2A, for example, first distance L1 may be approximately 133 mm; second distance L2 may be approximately 84 mm; third distance L3 may be approximately 85 mm; and fourth distance L4 may be approximately 413 mm.

Various ratios are defined in this example, and the ratios may be applied to other iterations of system 100. For example, as demonstrated, the curvature radius of reflective surface 112A may be approximately one third the curvature radius of reflective surface 117; first distance L1 may be approximately equal to second distance L2; and fourth distance L4 may be greater than the sum of distances L1, L2 and L3.

Similar to above, relay assembly 112 and galvo 116 may improve beam quality by reducing the BPP of input laser beam 2A and/or combined laser beam 4 at various points within system 1. For example, reflective surfaces 112A and 114A, reflective surface 117, the respective distances L1, L2, L3, and L4 extending therebetween, and coupling assembly 20 may minimize the BPP of combined beam 4 at input surface 41 of optical fiber 40, ensuring high beam quality. Alignment tolerances also may be increased in system 100. The BPP of combined laser beam 4 within system 100 may be at least 20% less than the BPP of optical fiber 40 at input surface 41. For example, the BPP of combined laser beam 4 at input surface 41 may be approximately 54 mm-mrad, and the BPP of fiber 40 at surface 41 may be approximately 68 mm-rad, providing for a BPP reduction of approximately 23%.

Laser system 200 is modified to utilize more conventional components. As shown in FIG. 2B, laser system 200 may comprise plurality of laser resonators 210, a relay assembly 212, and a galvo 216 with a reflective surface 217. The plurality of resonators 210 may be identical to resonators 10A-D described above. Only laser resonator 210A and input laser beam 2A are shown in FIG. 2B for ease of description. Similar configurations may be used for additional laser input beams (e.g., from laser generators 10B, 10C, and 10D). As shown, laser resonator 210A of system 200 may have a curved output surface 208A, and input laser beam 2A may be discharged through surface 208A. Curved output surface 208A may be a plano-convex lens that reduces the size of input laser beam 2.

Figure 2B:
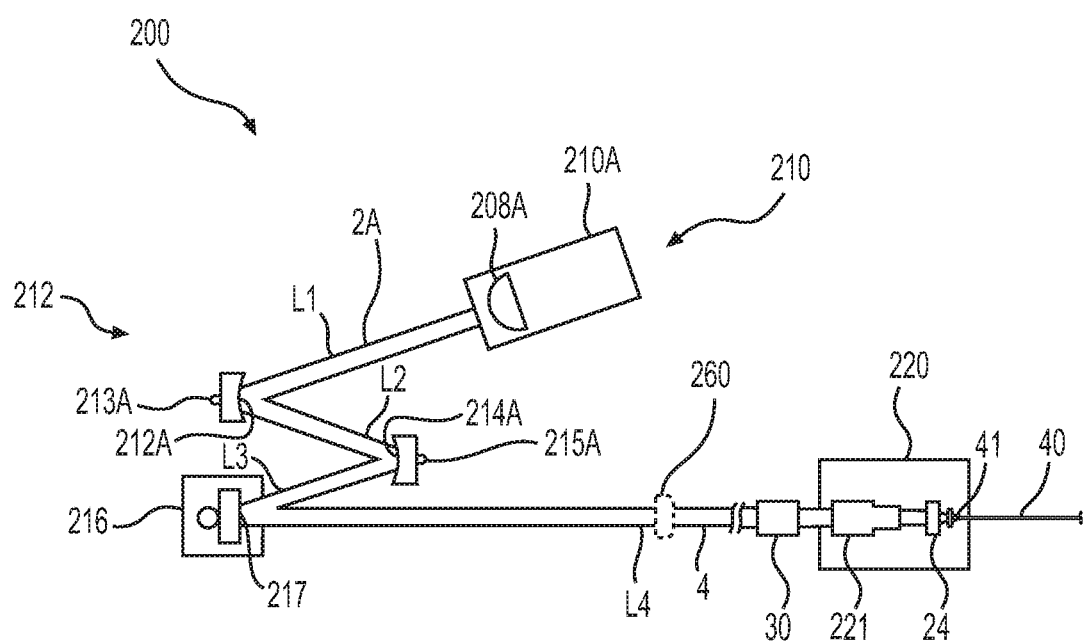
FIG. 2B depicts yet another laser system according to this disclosure.

Relay assembly 212 of FIG. 2B includes a first reflective surface 212A movably mounted to surface 7 by a tilt mount 213A, and a second reflective surface 214A movably mounted to surface 7 by a tilt mount 215A. First reflective surface 212A may modify beam 2A, and redirect the modified beam 2A towards second reflective surface 214A. Second reflective surface 214A may further modify beam 2A, and redirect the further modified beam 2A towards reflective surface 217. As shown in FIG. 2B, the first and second reflective surfaces 212A and 214A may be curved; and reflective surface 117 may be a flat. Optical assembly 30 may be included within system 200. A coupling assembly 220 is included within system 200.

The curvature of curved output surface 208A may be relative to the curvature of reflective surfaces 212A and 214A. For example, the curvature radius curved output surface 208A may be approximately 800 mm; the curvature radius of first reflective surface 212A may be approximately 300 mm; and the curvature radius of second reflective surface 214A may be approximately 400 mm. As before, the curvatures within system 200 also may be relative to the respective distances L1, L2, L3, or L4 between laser generator 10A, surfaces 212A and 214A, reflective surface 217, and input surface 41 of optical fiber 40. Distances L1-L4 in system 200 are similar to their counterpart distances described above in system 100. Throughout system 200, first distance L1 may be approximately equal to 133 mm; second distance L2 may be approximately equal to 84 mm; third distance L3 may be approximately equal to 86 mm; and fourth distance L4 may be approximately equal to 450 mm. Once again, various ratios may be defined between the curvatures and distances, and said ratios may be used to accommodate variations of laser system 200.

Relay assembly 212 and galvo 216 may improve beam quality by reducing the BPP of input laser beam 2A and combined laser beam 4 within system 1. For example, reflective surfaces 212A, 214A, and 217, the respective distances L1, L2, L3, and L4 extending therebetween may minimize the BPP of combined beam 4 at input surface 41 of optical fiber 40, ensuring high beam quality. Accordingly, reflective surface 217 and coupling assembly 220 may be conventional, off the shelf components, such as a fiber coupler 221. Alignment tolerances may be increased in system 200. The BPP of combined laser beam 4 within system 200 may at least 10% less than the BPP of optical fiber 40 at input surface 41. For example, the BPP of combined laser beam 4 at input surface 41 may be approximately 58 mm-mrad, and the BPP fiber 40 at surface 41 may be approximately 68 mm-rad, providing for a BPP reduction of about 16%.

Distances L1, L2, L3, and L4 may vary. In system 200, for example, the fourth distance L4 may be increased to accommodate additional components of optical assembly 30, such as additional shuttering mechanism operable to pulse combined laser beam 4. Increasing fourth distance L4 may cause the beam size of laser beam 4 to expand, potentially increasing the BPP of beam 4. System 200 may be further modified to address this issue. For example, as shown in FIG. 2B, a spherical relay lens 260 may be placed in the path of combined laser beam 4 to reduce the beam size of beam 4 on coupling assembly 220. Systems 1 and 100 may be similarly modified.

To maintain beam quality, the curvatures and distances within modified system 200 may be relative to the location and effective focal length of spherical relay lens 260. For example, when spherical relay lens 260 is placed 200 mm away from galvo 216 and has an effective focal length of 250 mm, the curvature radius of curved output surface 208A may be approximately 200 mm; the curvature radius of first reflective surface 212A may be approximately 300 mm; and the curvature radius of second reflective surface 214A may be approximately 500 mm; first distance L1 may be approximately equal to 133 mm; second distance L2 may be approximately equal to 81 mm; third distance L3 may be approximately equal to 90 mm; and fourth distance L4 may be approximately equal to 600 mm. Various ratios may be defined and applied based on this example.

Alignment tolerances may be improved by modified system 200. For example, because of spherical relay lens 260, the BPP of combined laser beam 4 within modified system 200 may still be at least 10% less than the BPP of optical fiber 40 at input surface 41, despite the increases to fourth distance L4. The BPP of combined laser beam 4 at input surface 41 may be approximately 57 mm-mrad, and the BPP fiber 40 at surface 41 may be approximately 68 mm-rad, providing a BPP reduction of about 18%. As demonstrated, the diameter of curved output surface 208A also may be reduced when lens 260 is used, reducing the size of laser resonator 210A.

Figure 3:
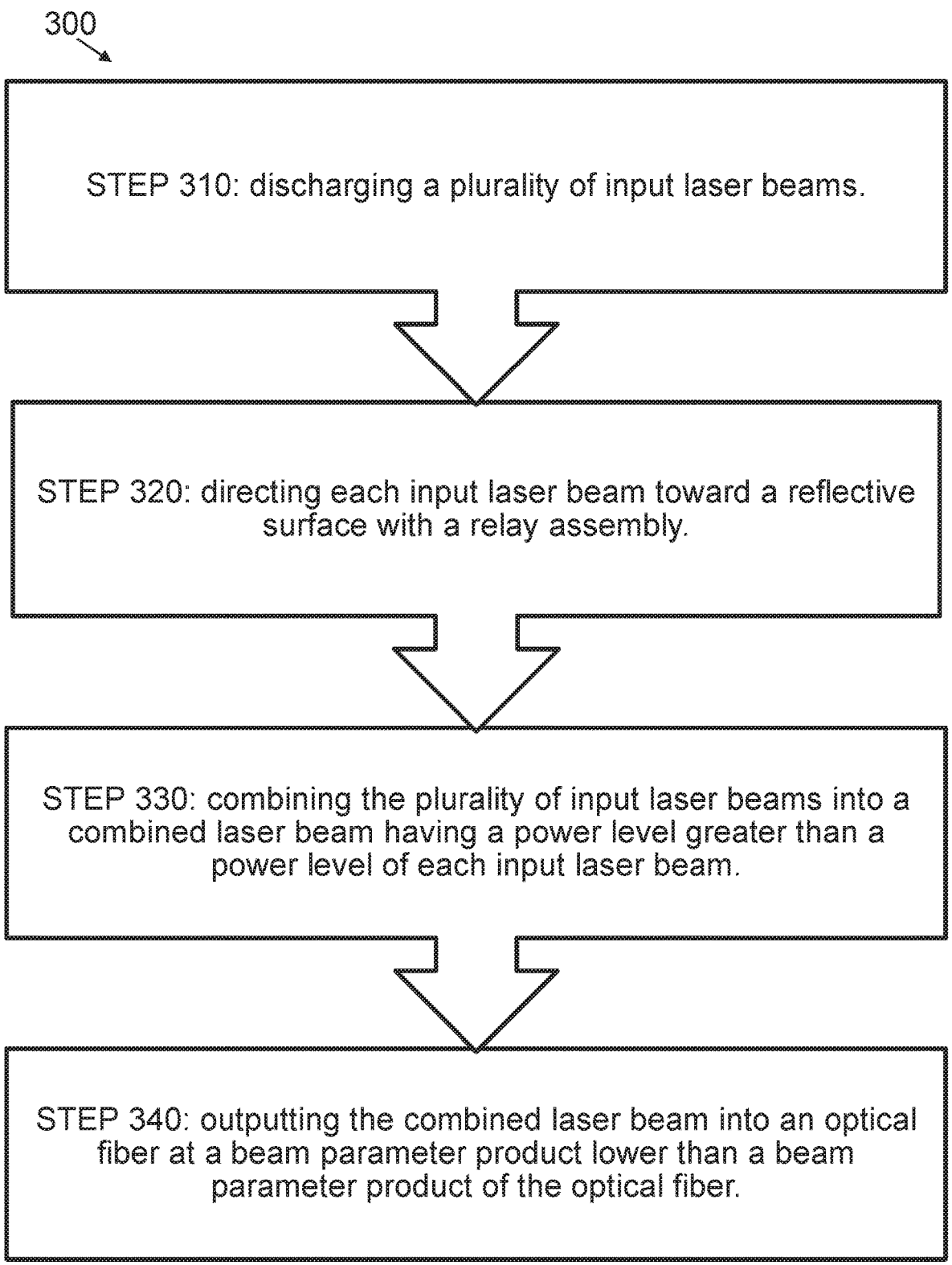
FIG. 3 depict a method according to this disclosure.

A method 300 is now described with reference to laser system 1, although similar methods are applicable to systems 100 and 200. As shown in FIG. 3, method 300 may comprise: discharging a plurality of input laser beams 2A-D (a "discharging" step 310); directing each input laser beam 2A-D toward reflective surface 17 with relay assembly 12 (a "directing" step 320); and rotating the curved reflective surface 17 to output combined laser beam 4 at a power level greater than a power level of each input laser beam 2A-D (a "combining" step 330); and outputting the combined laser beam 4 into optical fiber 40 at a BPP lower than a BPP of the fiber 40 (an "outputting" step 340). Additional aspects of steps 310, 320, 330, and 340 are now described in greater detail.

Discharging step 310 may comprise any intermediate steps for configuring and operating plurality of laser resonators 10 or 210. With laser system 1 of FIG. 1, for example, step 310 may comprise determining the laser settings necessary to discharge input laser beams 2A-D. For each input laser beam within laser system 200 of FIG. 2B, wherein second reflective surface 214A is curved, reflective surface 217 is flat, discharging step 310 may further comprise step similar to discharging input laser beam 2A through curved output surface 208A.

Directing step 320 may comprise any intermediate steps for configuring relay assemblies 12, 112, and 212. With system 1 of FIG. 1, for example, step 320 may comprise operating tilt plates 11A-D and/or tilt mounts 13A-D to align laser resonators 10A-D with reflective surfaces 12A-D so that each input laser beam 2A-D is directed towards reflective surface 17. For each laser input beam within systems 100 and 200, step 320 may comprise attaching laser resonator 110A or 210A to surface 7, and operating tilt mounts 113A, 213A and 115A, 215A to align laser resonator 10A with reflective surface 117 or 217.

Directing step 320 may be modified to account for the curvature of the various reflective surfaces and lenses described herein. For example, step 320 may further comprise reducing the beam size of and/or removing spherical aberrations from each input laser beam 2A-D. In system 1, for example, both reflective surfaces 12A and 17 are curved reflective surfaces, and step 330 may comprise directing the laser beams with the curved reflective surfaces. Similar intermediate steps may be performed with systems 100 and 200. With those systems, for example, step 330 may comprise: directing input laser beam 2 towards first reflective surface 112A or 212A; reducing the beam size of beam 2A with surfaces 112A or 212A; directing beam 2A from surfaces 112A or 212A toward second reflective surfaces 114A or 214A; and directing beam 2A from second reflective surface 114A or 214A to reflective surface 117.

Combining step 330 may comprise any means for generating combined laser beam 4, including the use of galvo 16 and like technologies. Within method 300, for example, step 330 may comprise any intermediate steps for configuring galvos 16, 116, and 216, such as determining the rotational speed of corresponding reflective surfaces 17, 117, and 217. Step 330 may further comprise reducing spherical aberrations in combined laser beam 4. For example, step 330 may comprise directing combined laser beam 4 through coupling assembly 20. Step 330 also may include steps for outputting combined laser beam 4 through a spherical relay lens. With system 200, for example, step 330 may comprising outputting combined laser beam 4 through spherical relay lens 260 to reduce the beam size of combined beam 4 on fiber coupler 221.

Outputting step 340 may comprise any intermediate steps for outputting combined laser beam 4 onto input surface 41 of optical fiber 40, including any steps for outputting beam 4 at a BPP lower than a BPP of input surface 41. Within system 1, for example, step 340 may comprise steps for directing combined laser beam through optical assembly 30, and/or realizing any benefits of assembly 30. For example, step 340 may comprise using first beam splitter 31 to direct a portion of combined laser beam 4 towards a controller; operating shutter mechanism 32 in response to an output signal from said controller; using second beam splitter 31 to direct an aiming beam toward input surface 41 of optical fiber 40; and/or directing combined laser beam 4 through black shield 24. Any optics may be utilized in step 340.

According to this description, systems 1, 100, and 200, as well as method 300, may be used to generate combined laser beam 4 from a plurality of input laser beams 2A-D, and output combined laser beam 4 with (i) an average power level equal to the sum of the power levels of each input laser beam 2A-D, and (ii) a BPP that is at least 10% less than a BPP of optical fiber 40. The BPP of the optical fiber may be defined by a minimum diameter of fiber 40 at input surface 41, or based on another minimum diameter of optical fiber 40 at different location. In most laser systems, the minimum diameter of the optical fiber 40 is determined by other system requirements, making systems 1, 100, and 200 and method 300 particularly useful for increasing alignment tolerances and reducing the risk of component failure.

Numerous aspects of this disclosure are described with reference to specific examples of systems 1, 100, and 200. Dimensions and ratios are provided in these specific examples to support a completed understanding of this disclosure. Unless claimed, these dimensions and ratios are not intended to limit this disclosure.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. A laser system comprising:
   a plurality of laser resonators, each resonator configured to discharge an input laser beam;
   a relay assembly including at least one reflective surface that redirects each input laser beam;
   a galvo mirror including a reflective surface that receives each redirected beam, and outputs a combined laser beam at a power level greater than a power level of each laser input beam; and
   a coupling assembly configured to direct the combined laser beam into an optical fiber,
   wherein each input laser beam is configured to be discharged along a beam path comprising: (i) a first distance extending from one resonator of the plurality of laser resonators to the at least one reflective surface of the relay assembly; and (ii) a second distance extending from the at least one reflective surface of the relay assembly to the reflective surface of the galvo mirror, and wherein the first distance is approximately equal to the second distance.

2. The laser system of claim 1, wherein the at least one reflective surface of the relay assembly is curved or flat.

3. The laser system of claim 1, wherein the reflective surface of the galvo mirror is curved or flat.

4. The laser system of claim 1, further comprising a surface onto which each of the plurality of laser resonators is movably mounted.

5. The laser system of claim 4, wherein each of the plurality of laser resonators is movably mounted onto the surface via a tilt plate.

6. The laser system of claim 4, wherein the at least one reflective surface is movably mounted onto the surface via a tilt mount, wherein the tilt mount is movable in at least two degrees of freedom relative to the surface.

7. The laser system of claim 1, wherein the reflective surface of the galvo mirror is rotatable relative to the laser system.

8. The laser system of claim 1, wherein the combined laser beam has a maximum beam parameter product lower than a minimum beam parameter product of the optical fiber.

9. The laser system of claim 1, wherein the coupling assembly outputs the combined laser beam onto an input surface of the optical fiber, and a beam parameter product of the combined laser beam is at least 10% less than a beam parameter product of the optical fiber at the input surface.

10. A laser system comprising:
    at least one laser resonator being operable to discharge an input laser beam;
    a relay assembly including a first reflective surface and a second reflective surface, both of which redirect the input laser beam; and
    a galvo mirror including a third reflective surface that receives the redirected beam;
    wherein the first reflective surface has a first curvature radius, the third reflective surface has a second curvature radius, and the first curvature radius is approximately one third the second curvature radius.

11. The laser system of claim 10, wherein the input laser beam is configured to be discharged along a beam path comprising: (i) a first distance extending from the at least one resonator to the first reflective surface of the relay assembly; (ii) a second distance extending from the first reflective surface to the second reflective surface of the relay assembly; (iii) a third distance extending from the second reflective surface to the third reflective surface.

12. The laser system of claim 11, wherein the beam path further comprises (iv) a fourth distance extending from the third reflective surface to an optical fiber.

13. The laser system of claim 11, wherein the second distance is approximately equal to the third distance.

14. The laser system of claim 11, wherein the at least one laser resonator includes a curved output surface having a third curvature radius, and wherein the first curvature radius is approximately one third the third curvature radius.

15. A method comprising:
    discharging input laser beams from a plurality of laser resonators;
    directing each input laser beam towards a relay assembly including at least one reflective surface that redirects the beam toward a reflective surface of a galvo mirror;
    combining the input laser beams, with the reflective surface of the galvo mirror, into a combined laser beam, and
    outputting the combined laser beam to an optical fiber,
    wherein each input laser beam is discharged along a beam path comprising: (i) a first distance extending from one resonator of the plurality of laser resonators to the at least one reflective surface of the relay assembly; (ii) a second distance extending from the at least one reflective surface of the relay assembly to the reflective surface of the galvo mirror; and (iii) a third distance extending from the reflective surface of the galvo mirror to the optical fiber,
    wherein the first distance is approximately equal to the second distance.

16. The method of claim 15, wherein the reflective surface of the galvo mirror is curved or flat, and the at least one reflective surface of the relay assembly is curved or flat.

17. The method of claim 15, further comprising rotating the reflective surface of the galvo mirror to output the combined laser beam at a power level greater than a power level of each input laser beam.

18. The method of claim 15, further comprising aligning the plurality of laser resonators with the at least one reflective surface to direct each input laser beam towards the relay assembly.

19. The method of claim 15, wherein the combined laser beam is outputted onto an input surface of the optical fiber, and a beam parameter product of the combined laser beam is at least 10% less than a beam parameter product of the optical fiber at the input surface.

20. The method of claim 15, wherein the combined laser beam has a power level greater than a power level of each input laser beam.

* * * * *